United States Patent [19]
Ito et al.

[11] Patent Number: 5,162,582
[45] Date of Patent: Nov. 10, 1992

[54] N-(2-METHOXYETHYL)-N-ISOPROPYLA-CRYLAMIDE, HYDROPHILIC-HYDROPHOBIC THERMALLY REVERSIBLE MACROMOLECULAR COMPOUND, METHOD FOR PRODUCTION THEREOF, AND THERMALLY REVERSIBLE MACROMOLECULAR COMPOSITION

[75] Inventors: Shoji Ito; Okihiko Hirasa; Shoei Fujishige; Aizo Yamauchi, all of Tsukuba, Japan

[73] Assignees: Agency of Industrial Science and Technology; Minstry of International Trade and Industry, Tokyo, Japan

[21] Appl. No.: 472,814

[22] Filed: Jan. 31, 1990

[30] Foreign Application Priority Data

Feb. 15, 1989 [JP] Japan .................................. 1-35758

[51] Int. Cl.⁵ .................. C07C 221/00; C07C 233/01; C08F 20/58; C08F 22/38
[52] U.S. Cl. ..................................... 564/208; 526/304
[58] Field of Search ........................................ 564/208

[56] References Cited

U.S. PATENT DOCUMENTS 4,134,916  1/1979  Moss et al. .......................... 564/208

OTHER PUBLICATIONS

The Society of Polymer Science, Japan, vol. 46, No. 7, pp. 437-443, Jul. 1989.

*Primary Examiner*—Paul R. Michl
*Assistant Examiner*—Tae H. Yoon
*Attorney, Agent, or Firm*—Oblon, Spivak, McClelland, Maier & Neustadt

[57] ABSTRACT

N-(2-methoxyethyl)-N-isopropylacrylamide is a novel compound. The polymer obtained by polymerizing this novel compound is a novel hydrophilic-hydrophobic thermally reversible type macromolecular compound having a transition temperature in the range of 12° C. to 14° C.

6 Claims, 1 Drawing Sheet

N-(2-METHOXYETHYL)-N-ISOPROPYLACRYLAMIDE, HYDROPHILIC-HYDROPHOBIC THERMALLY REVERSIBLE MACROMOLECULAR COMPOUND, METHOD FOR PRODUCTION THEREOF, AND THERMALLY REVERSIBLE MACROMOLECULAR COMPOSITION

BACKGROUND OF THE INVENTION

1. Field of the Invention

This invention relates to a novel vinyl compound, a hydrophilic-hydrophobic thermally reversible macromolecular compound, a method for the production of the compound, and a thermally reversible type macromolecular composition. More particularly, this invention relates to a vinyl compound usable for the production of a hydrophilic-hydrophobic thermally reversible macromolecular compound, a hydrophilic-hydrophobic thermally reversible macromolecular compound useful as material for light shields, temperature sensors, adsorbents, toys, interior materials, pastes for resist printing, displays, separation membranes, and mechanochemical materials, a method for efficient production of the compound, and a thermally reversible macromolecular composition containing the macromolecular compound.

2. Prior Art Statement

Some of the water-soluble macromolecular compounds exhibit a specific behavior of reversible solubility, i.e. a phenomenon in which such a compound on being mixed with water is precipitated and consequently caused to opacify the aqueous medium at a specific temperature (transition temperature or clouding point) and is dissolved and allowed to clarify the aqueous medium at a temperature below the specific temperature. These water-soluble macromolecular compounds are called hydrophilic-hydrophobic thermally reversible macromolecular compounds and have attracted attention in recent years for their usefulness as mechanochemical materials, pastes for resist printing, and separation membranes.

The thermally reversible macromolecular compounds of the foregoing type heretofore known to the art as include partially saponified polyvinyl acetate, polyvinyl methyl ether, methyl cellulose, polyethylene oxide, polyvinyl methyloxazolidinone, and polyacrylamide derivatives.

Among the thermally reversible macromolecular compounds mentioned above, polyacrylamide derivatives are particularly useful because they are stable in water and producible relatively inexpensively. Specifically, poly-N-ethylacrylamide, poly-N-n-propyl(meth)acrylamides, poly-N-isopropyl(meth)acrylamides, poly-N-cyclopropyl(meth)acrylamides, poly-N,N-diethylacrylamide, poly-N-methyl-N-ethylacrylamide, poly-N-methyl-N-n-propylacrylamide, poly-N-methyl-N-isopropylacrylamide, poly-N-acryloylpiperidine, poly-N-acryloylpyrrolidine, poly-N-tetrahydrofurfuryl(meth)acrylamide, poly-N-methoxypropyl(meth)acrylamide, poly-N-ethoxypropyl(meth)acrylamide, poly-N-isopropoxypropyl(meth)acrylamide, poly-N-ethoxyethyl(meth)acrylamide, poly-N-(2,2-dimethoxyethyl)-N-methylacrylamide, poly-N-1-methyl-2methoxyethyl(meth)acrylamide, poly-N-1-methoxymethylpropyl(meth)acrylamide, poly-N-(1,3-dioxolan-2-yl)-N-methylacrylamide, and poly-N-8-acryloyl-1,4-dioxa-8-azaspiro[4.5]decane, are known for example.

Ito, one of the inventors of the subject patent application, is also a co-inventor of a hydrophilichydrophobic thermally reversible type polymer having repeating units of the following formula and the invention has been patented under U.S. Pat. No. 4,822,848.

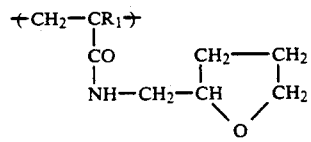

These thermally reversible macromolecular compounds have transition temperatures in specific ranges of their own. It has been desired to develop a thermally reversible macromolecular compound having a transition point over a wider range suitable for practical purposes.

An object of this invention is to provide a thermally reversible macromolecular compound having a transition temperature different from that of any of the conventional countertypes.

Another object of this invention is to provide a vinyl compound suitable for the production of the thermally reversible macromolecular compound mentioned above.

SUMMARY OF THE INVENTION

The inventors continued a study with a view to accomplishing the objects described above. They found consequently that a macromolecular compound comprising repeating units of the formula:

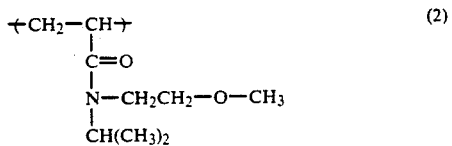

obtained by radically polymerizing a vinyl compound represented by the formula:

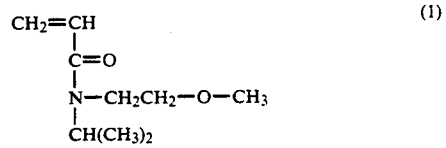

and having a molecular weight corresponding to an intrinsic viscosity [$\eta$] in the range of 0.01 to 6.0 as measured in a tetrahydrofuran solution at a temperature of 27° C. is a hydrophilic-hydrophobic thermally reversible macromolecular compound. This invention has been perfected based on this knowledge.

To be specific, this invention provides hydrophilic-hydrophobic thermally reversible macromolecular compound comprising repeating units represented by the formula:

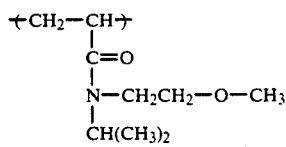

and having a molecular weight corresponding to an intrinsic viscosity [η] in the range of 0.01 to 6.0 as measured in a tetrahydrofuran solution at a temperature of 27° C., a method for the production thereof, a vinyl compound for the production of the hydrophilic-hydrophobic thermally reversible macromolecular compound, and a composition comprising the hydrophilic-hydrophobic thermally reversible macromolecular compound and water.

The above and other features and objects of the invention will become apparent with the following detailed description made with reference to the attached drawings.

DETAILED DESCRIPTION OF THE PREFERRED EMBODIMENT

Figure 1:
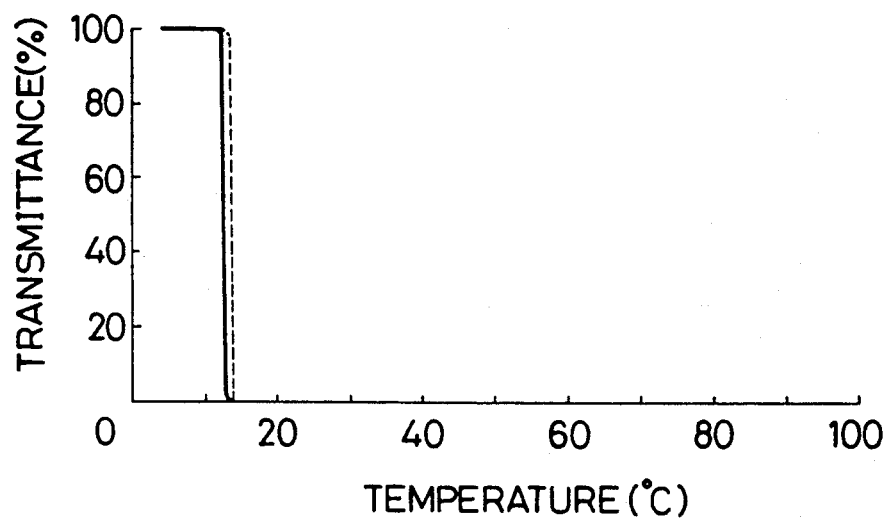
FIG. 1 is a diagram showing the relation between the transmittance and the temperature obtained of an aqueous 1 wt% solution of a hydrophilic-hydrophobic thermally reversible macromolecular compound of this invention obtained in Example 2.

The vinyl compound to be used in the present invention is N-(2-methoxyethyl)-N-isopropylacrylamide, i.e. a novel compound not reported in literature to date. This vinyl compound can be obtained by causing acryloyl chloride, N-(2-methoxyethyl)-isopropylamine, and triethylamine to react in a solvent kept at a temperature in the range of 0° C. to 10° C. in accordance with the reaction formula:

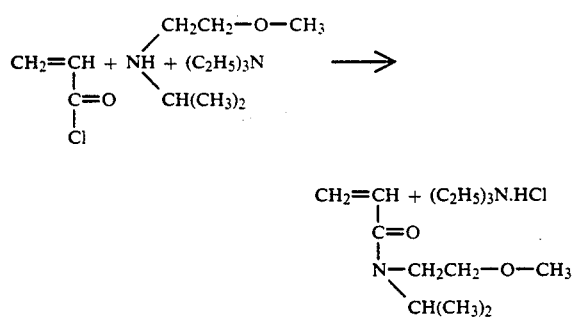

or by causing acryloyl chloride and N-(2-methoxyethyl)isopropylamine to react in a solvent kept at a temperature in the range of 0° C. to 10° C. in accordance with the reaction formula:

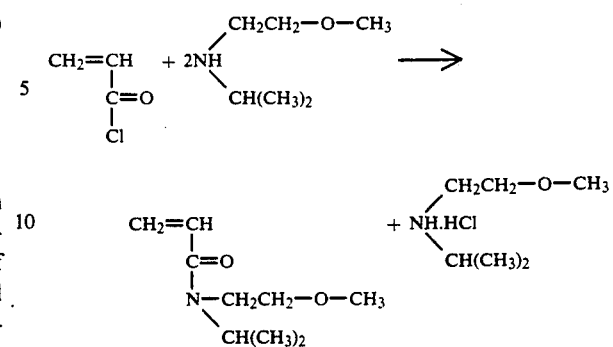

The solvent to be used in either of the methods described above has no particular restriction except for the sole requirement that it should be insoluble in acryloyl chloride. Generally, benzene, acetone, toluene, and the like are usable. Since the reaction entails a secondary reaction at unduly high reaction temperatures, it is desired to be carried out at a temperature in the range of 0° C. to 10° C.

By the reaction described above, a reaction solution containing the novel vinyl compound is obtained. Now, the method for isolating the novel vinyl compound from the reaction solution will be described below. The purified novel vinyl compound is obtained by removing triethylamine hydrochloride or N-(2-methoxyethyl)isopropylamine hydrochloride from the reaction solution by separating means such as filtering, distilling the resultant product with a rotary evaporator thereby expelling the solvent from the filtrate by distillation, and then subjecting the distillate to vacuum distillation. The distillate can be refined to higher purity by repeating the vacuum distillation.

The N-(2-methoxyethyl)-N-isopropylacrylamide which is consequently obtained is a colorless liquid (boiling point 98° C./2 mmHg) and is soluble in such solvents as water, methyl alcohol, ethyl alcohol, acetone, tetrahydrofuran, chloroform, carbon tetrachloride, and benzene.

Since the N-(2-methoxyethyl)-N-isopropylacrylamide contains a $CH_2=CH-$ group, a CON group, a $-CH_2-O-$ group, a $-CH_3$, and the like, it can be identified by the infrared absorption spectrum or the mass spectral analysis, for example.

The hydrophilic-hydrophobic thermally reversible macromolecular compound can be produced by subjecting this N-(2-methoxyethyl)-N-isopropylacrylamide to radical polymerization. The radical polymerization can be effected in the form of solution polymerization or bulk polymerization using a peroxide such as benzoyl peroxide or peracetic acid or an azo compound such as azobisisobutyronitrile as a polymerization initiator or resorting to irradiation with an active ray such as ultraviolet light, radiation, electron beam, or plasma. The amount of the polymerization initiator to be used is properly selected in the range of 0.005 to 5% by weight, preferably 0.001 to 2% by weight, based on the amount of the monomer.

Particularly desirably, the production of the hydrophilic-hydrophobic thermally reversible macromolecular compound is obtained by a method which comprises dissolving N-(2-methoxyethyl)-N-isopropylacrylamide in a concentration in the range of 1 to 80% by weight in an organic solvent and subjecting the resultant solution to solution polymerization.

The solvent to be used in this method of solution polymerization has no specific restriction except for the sole requirement that it should be capable of dissolving the N-(2-methoxyethyl)-N-isopropylacrylamide. The solvents which answer this description include water, alcohols, acetone, tetrahydrofuran, chloroform, carbon tetrachloride, benzene, and alkyl acetates, for example. These solvents may be used either singly or in the form of a mixture of two or more members.

Since the macromolecular compound of this invention contains a $CON<$ group, a $CH_2$—O— group, a CH group, and a —$CH_3$ group, it can be identified by the infrared absorption spectrum, for example.

For the produced polymer to be used practically, the degree of this polymerization is desired to be such as to equal an intrinsic viscosity $[\eta]$ in the range of 0.01 to 6.0 as measured in a tetrahydrofuran solution at 27° C. The macromolecular compound is soluble in cold water, alcohols such as methanol, ethanol, and isopropanol, acetone, tetrahydrofuran, dioxane, chloroform, benzene, and alkyl acetates such as, methyl acetate, ethyl acetate, n-propyl acetate, n-butyl acetate, sec-butyl acetate, tert-butyl acetate, n-amyl acetate, and n-hexyl acetate and insoluble in hot water, cyclohexane, n-hexane, and n-heptane, for example.

The macromolecular compound of this invention is a hydrophilic-hydrophobic thermally reversible type macromolecular compound which becomes soluble in water in a low temperature zone and insoluble in water in a high temperature zone. Though the transition temperature is variable with the conditions of polymerization, it generally falls in the range of 12° C. to 14° C.

The composition of this invention which essentially consists of the hydrophilic-hydrophobic thermally reversible macromolecular compound and water has a transition temperature generally in the range of 12° C. to 14° C.

The macromolecular compound of this invention is a novel macromolecular compound which has not yet been reported in literature. Specifically, this is a hydrophilic-hydrophobic thermally reversible type macromolecular compound which becomes soluble in water in a low temperature range and insoluble in water in a high temperature zone. Thus, it possesses a different transition temperature from that of any of the heretofore known thermally reversible polyacrylamide derivatives. Thus, it can be utilized for light shielding and temperature sensors in hothouses, chemical laboratories, and radioisotope laboratories, adsorbents in surfactants, toys, interior materials, pastes for resist printing, displays separation membranes, materials in mechanochemical elements, for example.

Now, the present invention will be described more specifically below with reference to working examples. It should be noted, however, that this invention is not limited in any respect by these examples.

EXAMPLE 1

In an Erlenmeyer flask having an inner volume of 1 liter, 88.32 g of triethylamine, 101.96 g of N-(2-methoxyethyl)-isopropylamine, and 950 ml of toluene were kept cooled and, at the same time, stirred at a temperature of lower than 10° C. and, in the meantime, a mixed liquid consisting of 71 ml of acrylic acid chloride and 50 ml of toluene was added dropwise to the stirred mixture through a dropping funnel over a period of about 3 hours. After the dropwise addition was completed, the reaction solution was left reacting overnight in a refrigerator. The resultant reaction solution was filtered, the resultant filtrate was distilled with a rotary evaporator to expel toluene by distillation, and the distillate was subjected to vacuum distillation, to obtain 128.4 g of a colorless transparent fraction (boiling point 96° C./2 mmHg).

This fraction was spectrally analyzed. The results were as shown below.

| | m/e |
|---|---|
| Mass spectrum: | |
| M + 1 = | 172 |
| M = | 171 |
| M— —$CH_2$—O—$CH_3$ = | 126 |
| —$CH_2$—N—$CH_2$ $CH_2$—O— = | 72 |
| $CH_2$=CH—CO— = | 55 |
| $CH_2$=CH— = | 27 |
| Infrared absorption spectrum: | |
| —N< = | 3480 cm$^{-1}$ |
| $CH_2$=CH— = | 1605 cm$^{-1}$ |
| —O— = | 1110 cm$^{-1}$ |
| >C=O = | 1640 cm$^{-1}$ |
| >CH— = | 2960, 2930 cm$^{-1}$ |

From the results of analysis given above, the product was identified as N-(2-methoxyethyl)-N-isopropylacrylamide.

EXAMPLE 2

In a sealed tube having an inner volume of 30 ml, 20 ml of methanol, 4.81 g of N-(2-methoxyethyl)-N-isopropylacrylamide, and 49.7 mg of azobisisobutyronitrile were dissolved in one another. The resultant solution was repeatedly cooled and deaerated by the use of liquefied nitrogen and, with the tube sealed tightly, left reacting at a polymerization temperature of 60° C. for 8 hours in a constant temperature bath. After the reaction was completed, the reaction solution was left precipitating in a large volume of water at a temperature of not lower than 30° C. to cause isolation of the reaction product. Thus, 4.78 g of the reaction product was obtained.

The infrared absorption spectrum of the reaction product was compared with that of N-(2-methoxyethyl)-N-isopropylacrylamide. The comparison showed that reaction product was missing the 1,605 cm$^{-1}$ peak indicating the vinyl group, whereby formation of a macromolecular compound represented by the aforementioned formula (2) was confirmed.

The produced macromolecular compound was tested for intrinsic viscosity with an Ubbelohdes' viscometer using tetrahydrofuran as a solvent at 27° C. Thus, the intrinsic viscosity $[\eta]$ was found to be 0.24.

The transmittance-temperature curve of an aqueous solution of 1% by weight of the macromolecular compound (the hydrophilic-hydrophobic thermally reversible type macromolecular composition of this invention consisting of the macromolecular compound and water) is shown in FIG. 1. In the graph, the continuous line represents the data obtained during the rise of the temperature and the broken line that during the fall of the temperature. The transition temperature was found from the temperature, $T_L$, at which the transmittance of light fell to 0.5 of the initial transmittance. Thus, the transition temperature, $T_L$, was found to be 12.8° C.

EXAMPLE 3

In a four-neck flask having an inner volume of 1,000 ml and provided with a condenser, an argon inlet, and a stirrer, 500 ml of benzene, 30.64 g of N-(2-methoxyethyl)-N-isopropylacrylamide, and 0.1002 g of azobisisobutyronitrile were kept stirred and, at the same time, argon gas was bubbled through the stirred mixture for about two hours. Then, the resultant mixture and 100 ml of benzene containing 0.1002 g of azobisisobutyronitrile added thereto were left reacting in a constant temperature bath at 64° C. for 3 hours. After the reaction was completed, the reaction solution was treated with a rotary evaporator to expel about 400 ml of benzene and then mixed with n-hexane for isolation of the produced polymer. Thus, the polymer was obtained in a yield of 26.55 g.

Figure 2:
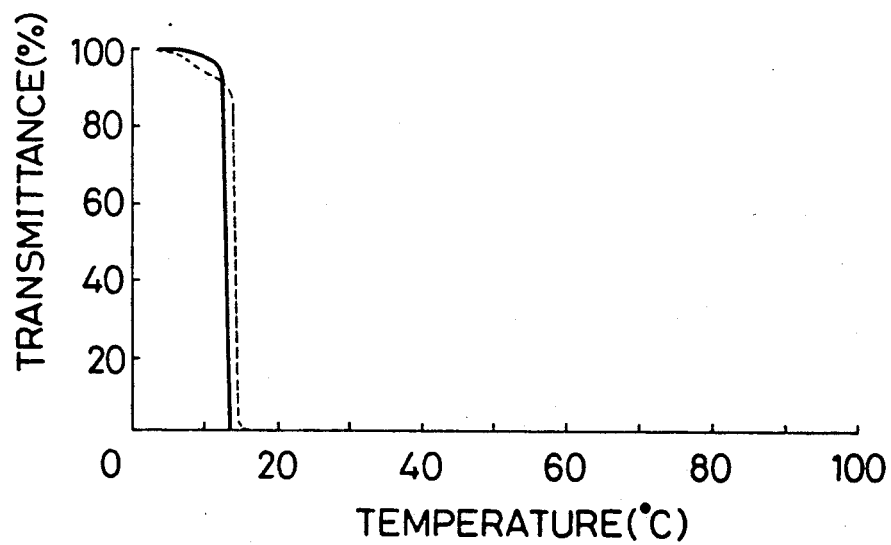
FIG. 2 is a diagram showing the relation between the transmittance and the temperature obtained of an aqueous 1 wt% solution of a hydrophilic-hydrophobic thermally reversible macromolecular compound of this invention obtained in Example 3.

In the same manner as in Example 1, the formation of a macromolecular compound of the formula (2) was confirmed. The transmittance-temperature curve of an aqueous solution of 1% by weight of the macromolecular compound (the hydrophilic-hydrophobic thermally reversible type macromolecular composition of this invention consisting of the macromolecular compound and water) is shown in FIG. 2. In the graph, the continuous line represents the data obtained during the rise of temperature and the broken line that during the fall of the temperature.

The produced macromolecular compound was tested for intrinsic viscosity and transition temperature by following the procedure of Example 1. Thus, the intrinsic viscosity $[\eta]$ was found to be 0.46 and the transition temperature, $T_L$, to be 13.0° C.

What is claimed is:

1. N-(2-methoxyethyl)-N-isopropylacrylamide represented by the formula:

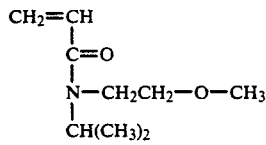

2. A hydrophilic-hydrophobic thermally reversible type macromolecular compound comprising repeating units represented by the formula:

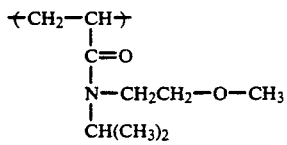

and having a molecular weight equivalent to an intrinsic viscosity $[\eta]$ in the range of 0.01 to 6.0 as measured in a tetrahydrofuran solution at a temperature of 27° C.

3. A method for the production of a hydrophilic-hydrophobic thermally reversible type macromolecular compound comprising repeating units represented by the formula:

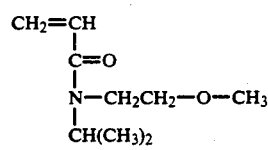

and having a molecular weight equivalent to an intrinsic viscosity $[\eta]$ in the range of 0.01 to 6.0 as measured in a tetrahydrofuran solution at a temperature of 27° C., which method essentially consists of radically polymerizing N-(2-methoxyethyl)-N-isopropylacrylamide represented by the formula:

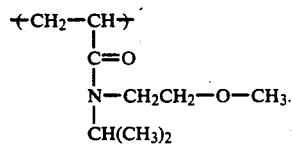

4. A method according to claim 3, wherein said polymerization is effected in the form of solution polymerization using N-(2-methoxyethyl)-N-isopropylacrylamide dissolved in an organic solvent in a concentration int he range of 1 to 80% by weight.

5. A hydrophilic-hydrophobic thermally reversible composition, essentially consisting of a hydrophilic-hydrophobic thermally reversible type macromolecular compound comprising repeating units represented by the formula:

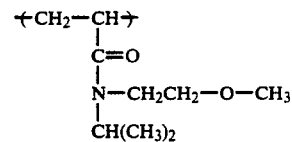

and having a molecular weight equivalent to an intrinsic viscosity $[\eta]$ in the range of 0.01 to 6.0 as measured in a tetrahydrofuran solution at a temperature of 27° C. and water, said polymer being soluble in water at temperatures below a transition temperature wherein a transparent aqueous solution of the polymer is produced, said polymer being insoluble in water at temperature above said transition temperature wherein an opaque, aqueous composition of the polymer is produced.

6. A composition according to claim 5, wherein the concentration of said polymer is 1% and the transition temperature is in the range of 12° C. to 14° C.

* * * * *